(12) United States Patent
Keppler

(10) Patent No.: US 7,485,659 B2
(45) Date of Patent: Feb. 3, 2009

(54) ANTICANCER COMPOSITIONS, AND METHODS OF MAKING AND USING THE SAME

(75) Inventor: Bernhard Keppler, Hockenheim (DE)

(73) Assignee: Faustus Forschungs CIE, Translational Cancer Research GmbH (DE)

( * ) Notice: Subject to any disclaimer, the term of this patent is extended or adjusted under 35 U.S.C. 154(b) by 0 days.

(21) Appl. No.: 11/696,116

(22) Filed: Apr. 3, 2007

(65) Prior Publication Data

US 2007/0293557 A1 Dec. 20, 2007

Related U.S. Application Data

(60) Division of application No. 10/627,519, filed on Jul. 25, 2003, now Pat. No. 7,338,946, which is a continuation of application No. PCT/EP02/00863, filed on Jan. 28, 2002.

(30) Foreign Application Priority Data

Jan. 26, 2001 (DE) ................. 101 03 565

(51) Int. Cl.
*A61K 31/415* (2006.01)
*C07D 231/56* (2006.01)
(52) U.S. Cl. ................. 514/403; 514/492; 548/361.1
(58) Field of Classification Search ............. 514/403, 514/492; 548/361.1
See application file for complete search history.

(56) References Cited

U.S. PATENT DOCUMENTS 4,843,069 A 6/1989 Keller et al.

FOREIGN PATENT DOCUMENTS

WO WO 97/36595 A2 10/1997

OTHER PUBLICATIONS

F.T. Garson et al., "Comparative antitumor activity of ruthenium derivatives with 5'-deoxy-5-fluorouridine in chemically induced colorectal tumors in SD rats," *Cancer Chemother Pharmacol*, pp. 347-349 (1987).
B.K. Keppler et al., "New Ruthenium Complexes for the Treatment of Cancer," *Progress in Clinical Biochemistry and Medicine*, vol. 10, pp. 41-69 (1989).
H. Depenbrock et al., "Preclinical Activity of Trans-indazolium [Tetrachlorobisindazoleruthenate (III)] (NSC 666158; IndCR; KP 1019) Againt Tumour Colony-forming Units and Haematopoietic Progenitor Cells," *European Journal of Cancer*, vol. 33, No. 14, pp. 2404-2410 (1997).
A. Galeano et al., "Antitumor Activity of Some Ruthenium Derivatives in Human Colon Cancer Cell Lines in vitro," *Arzneim.-Forsch./Drug Res.*, 42, vol. 1, No. 6, pp. 821-824 (1992).

F. Kratz et al., "Protein-Binding Properties Of Two Antitumour Ru(III) Complexes To Human Apotransferring And Apolctoferrin," *Metal-Based Drugs*, vol. 1, Nos. 2-3, pp. 169-173 (1994).
F. Kratz et al., "Comparison Of The Antiproliferative Activity Of Two Antitumour Ruthenium(III) Complexes With Their Apotransferrin and Transferrin-Bound Forms in a Human Colon Cancer Cell Line," *Metal-Based Drugs*, vol. 3, No. 11, pp. 15-23 (1996).
Y.N. Vashisht Gopal et al., "Topoisomerase II poisoning by indazole and imidazole complexes of ruthenium," *J. Biosci*, vol. 26, No. 2, pp. 271-276 (2001).
Ernst D. Kreuser et al., "Synergistic Antitumor Interactions Between Newly Synthesized Ruthenium Complexes and Cytokines in Human Colon Carcinoma Cell Lines," *Seminars in Oncology*, vol. 19, No. 2 Suppl 3, pp. 73-81 (1992).
S. Pacor et al., "Antitumor action of mer-trichlorobis (dimethylsulphoxide) aminoruthenium (III) (BBR2382) in mice bearing lewis lung carcinoma," *Metal Ions in Biology and Medicine*, pp. 482-484 (1990).
F. Kralik et al., "Complex compounds of trivalent ruthenium with pyrazol and imidazol," *Collection Czechoslov. Chem. Commun.*, vol. 26, pp. 1298-1304 (1961).
B.K. Keppler et al., "Synthesis Molecular Structure, and Tumor-Inhibiting Properties of Imidazolium trans-Bis(imidazole) tetrachlororuthenate(III) and its Methyl-Substituted Derivatives," *Inorg. Chem.*, vol. 26, pp. 4366-4370 (1987).
Martin R. Berger et al., "Efficacy of New Ruthenium Complexes against Chemically Induced Autochthonous Colorectal Carcinoma in Rats," *Anticancer Res.*, vol. 9, pp. 761-766, (1989).
E. Alessio et al., "Carbonyl Derivatives of Chloride-Dimethyl Sulfoxide-Ruthenium(II) Complexes: Systhesis, Structural Characterization, and Reactivty of $Ru(CO)_x(DMSO)_{4-x}Cl_2$ Complexes ($_x$=1—3)," *Inorg. Chem.*, vol. 34, pp. 4722-4734. (1995).

(Continued)

*Primary Examiner*—Rei-tsang Shiao
(74) *Attorney, Agent, or Firm*—Perkins Coie LLP; James Zhu

(57) ABSTRACT

Compositions, containing a ruthenium(III) complex and a heterocycle, methods for their manufacture, medicament containing these compositions and a kit.

The invention relates to a composition (A), obtained by reacting a compound of the general formula (I)

$$M_{3-n-p-2pr}[RUX_{6-n-p-q-2r}B_n(H_2O)_p(OH)_q(O)_r]_{2r+1} \quad (I)$$

with a compound of the general formula (II)

$$B'(HX')_s \quad (II).$$

Furthermore, the invention relates to a composition (B), obtained by mixing a compound of the general formula (III)

$$(B'H)_{3-n-p-2pr}[RUX_{6-n-p-q-2r}B_n(H_2O)_p(OH)_q(O)_r]_{2r+1} \quad (III)$$

with a compound of the general formula (IV)

$$MX' \quad (IV).$$

10 Claims, 4 Drawing Sheets

OTHER PUBLICATIONS

Woflgang Peti et al., "Synthesis of Tumor-Inhibiting Complex Salts Containing the Anion trans-Tetrachlorobis(indazole)ruthenate(III) and Crystal Structure of the Tetraphenylphosphonium Salt," *Eur. J. Inorg. Chem.*, pp. 1551-1555, (1999).

B.K. Keppler et al., "New Tumor-Inhibiting Metal Complexes, Chemistry and Antitumor Properties," *Met-Based Drugs*, vol. 1, Nos. 2-3, pp. 145-150, (1994).

Matthias H. Seelig et al., "Antineoplastic activity of three ruthenium derivatives against chemically induced colorectal carcinoma in rats," *J. Cancer Res. Clin. Oncol.*, vol. 118, No. 3, pp. 195-200 (1992).

Michael J. Clark, "The Potential of Ruthenium in Anticancer Pharmaceuticals," *American Chemical Society Symp. Ser.*, pp. 157-180 (1980).

Keller et al., European Journal of Inorganic Chemistry (1999), (9), 1551-1555.

Djinovic, V., et al., "Novel ruthenium complex K2[Ru(dmgly)C14].2H2O is toxic to C6 astrocytoma cell line, but not to primary rat astrocytes," J. Inorg. Biochem., 98(12):2168-73 (Dec. 2004) (Abstract Only).

Van Rensburg, C.E., et al., "Cytotoxicity of a series of water-soluble mixed valent diruthenium tetracarboxylates," Anticancer Res., 22(2A):889-92 (Mar.-Apr. 2002) (Abstract Only).

Heffeter, P., et al., "Intrinsic and Acquired Forms of Resistance against the Anticancer ruthenium Compound KP1019 [Indazolium trans-[tetrachlorobis(1H-indazole)ruthenate (III)] (FFC14A)," The Journal of Pharmacology and Experimental Therapeutics, 312(1):281-289 (2005).

Gaiddon, C., et al., "Ruthenium (II)-Derived Organometallic Compounds Induce Cytostatic and Cytotoxic Effects on Mammalian Cancer Cell Lines through p53-Dependent and p53-Independent Mechanisms," The Journal of Pharmacology and Experimental Therapeutics, 315(3):1403-1411 (2005).

ANTICANCER COMPOSITIONS, AND METHODS OF MAKING AND USING THE SAME

CROSS-REFERENCE TO RELATED APPLICATIONS

This application is a divisional of U.S. application Ser. No. 10/627,519 filed on Jul. 25, 2003, now U.S. Pat. 7,338,946 which is a continuation of International Application No. PCT/EP02/00863, filed Jan. 28, 2002, the content of both of which is incorporated herein by reference in their entirety.

BACKGROUND OF THE INVENTION

This invention relates to compositions which include a ruthenium(III) complex and a heterocycle and also to their application as medicaments for the treatment of cancer illnesses.

The possible applicability of ruthenium complexes in the treatment of cancer illnesses has been discussed by M. J. Clarke, *ACS Symp. Ser.* 140 (1980) 157-180.

Complex compounds of trivalent ruthenium with pyrazol and imidazol have been described by F. Kralik et al., *Collection Czechoslov. Chem. Commun.* 26 (1961) 1298 and by B. K. Keppler et al., *Inorg. Chem.*, 26 (1987) 4366-4370.

Furthermore, ruthenium(III) complexes with indazol and dimethyl sulfoxide have been investigated by B. K. Keppler et al., *Anticancer Res.*, 9 (1989) 761-766, G. Mestroni et al., *J. Am. Chem. Soc.* 111 (1989) 7068-7071 and G. Mestroni et al., *Inorg. Chem.*, 34 (1995) 4722-4734.

The tumor-inhibiting properties of ruthenium(III) complexes with a basic heterocycle, such as indazol, are also described in *Eur. J. Inorg. Chem.* 1999, 9, pp. 1551-1555, *Met.-Based Drugs* 1994, 1 (2-3), pp. 145-150 and *J. Cancer Res. Clin. Oncol.* 1992, 118(3), pp. 195-2000.

In the U.S. Pat. No. 4,843,069 medicaments are described which contain ruthenium(III) complexes with a monocyclic or multi-cyclic basic heterocycle. The complexes are suitable for cancer therapy, but are difficult to dissolve in water and are therefore not lyophilisable.

To avoid this disadvantage, WO97/36595 discloses ruthenium(III) complexes with an alkali metal cation or with ammonia which are easily soluble in water and which are also effective in the treatment of cancer illnesses. However, these compounds have the disadvantage that they exhibit a lower effectiveness than ruthenium complexes according to U.S. Pat. No. 4,843,069.

BRIEF SUMMARY OF THE INVENTION

Therefore, the object of the invention is to avoid the disadvantages mentioned above and to provide a composition which is easily water-soluble and which exhibits a high effectiveness in the treatment of cancer illnesses.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings.

Figure 1:
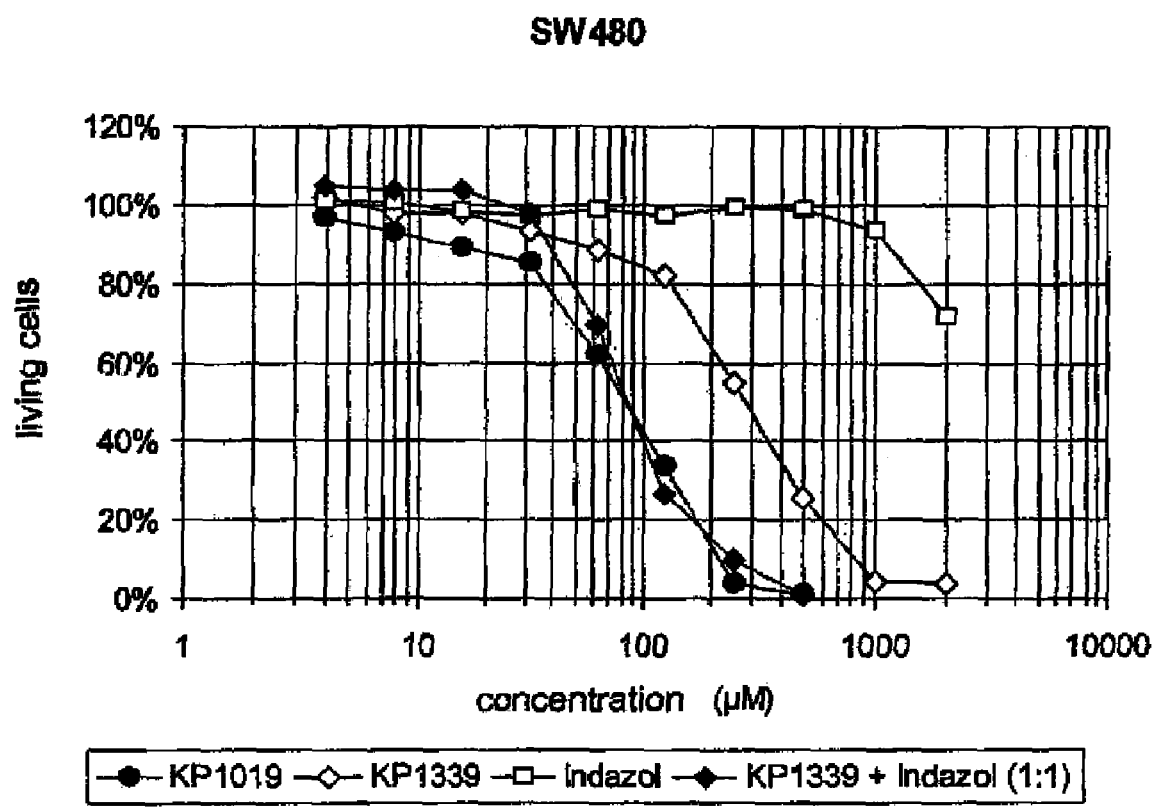
FIG. 1 shows a comparison of the cytotoxic effects of KP 1019, of the corresponding sodium salt KP 1339, indazol as well as the equimolar mixture of KP 1339 and indazol (administered as a solution in a conventional cell culture medium MEM, supplemented with 10% of fetal bovine serum, without the addition of organic solvents or dissolving agents) on the human line of tumor cells SW480 (colon carcinoma) in the MTT assay with continuous 96 hour exposure to the active substance.
Figure 2:
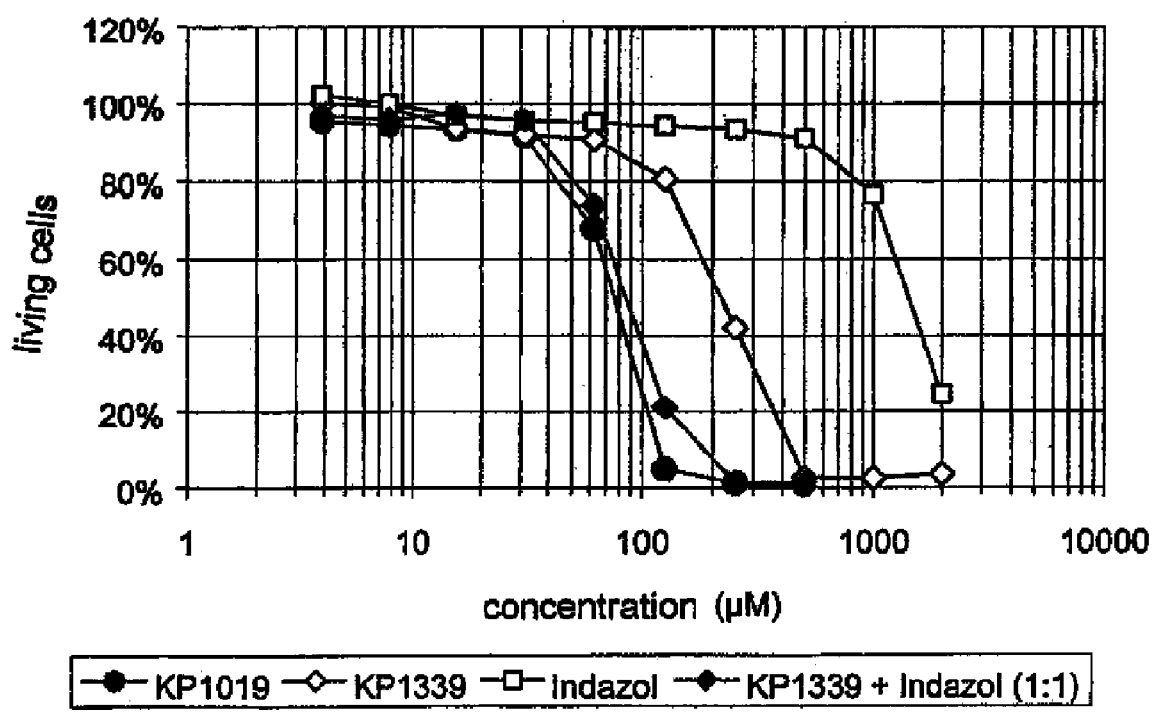
FIG. 2 shows a comparison of the cytotoxic effects of KP 1019, of the corresponding sodium salt KP 1339, indazol as well as the equimolar mixture of KP 1339 and indazol (administered as a solution in a conventional cell culture medium MEM, supplemented with 10% of fetal bovine serum, without the addition of organic solvents or dissolving agents) on the human line of tumor cells CH1 (ovarian carcinoma) in the MTT assay with continuous 96 hour exposure to the active substance.
Figure 3:
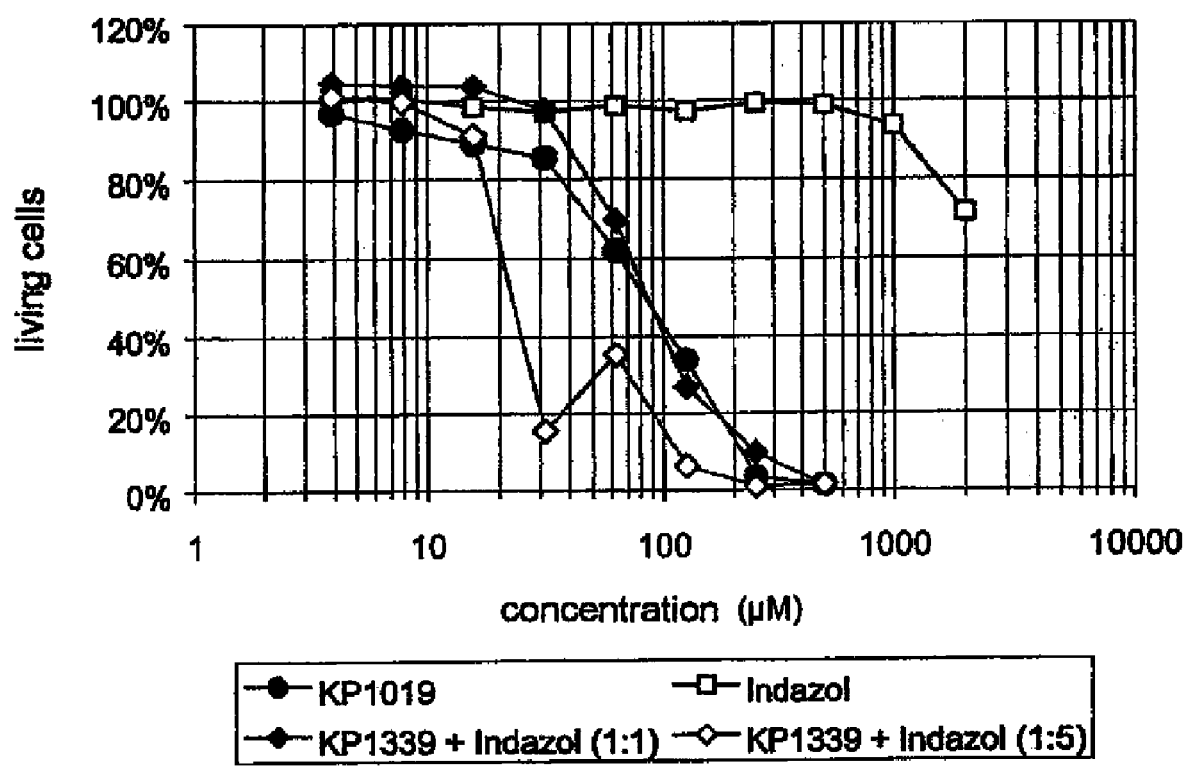
FIG. 3 shows a comparison of the cytotoxic effects of KP 1019, indazol, and of mixtures of KP 1339 and indazol in the molar ratios of 1:1 and 1:5 (administered as a solution in a conventional cell culture medium MEM, supplemented with 10% of fetal bovine serum, without the addition of organic solvents or dissolving agents) on the human line of tumor cells SW480 (colon carcinoma) in the MTT assay with continuous 96 hour exposure to the active substance.
Figure 4:
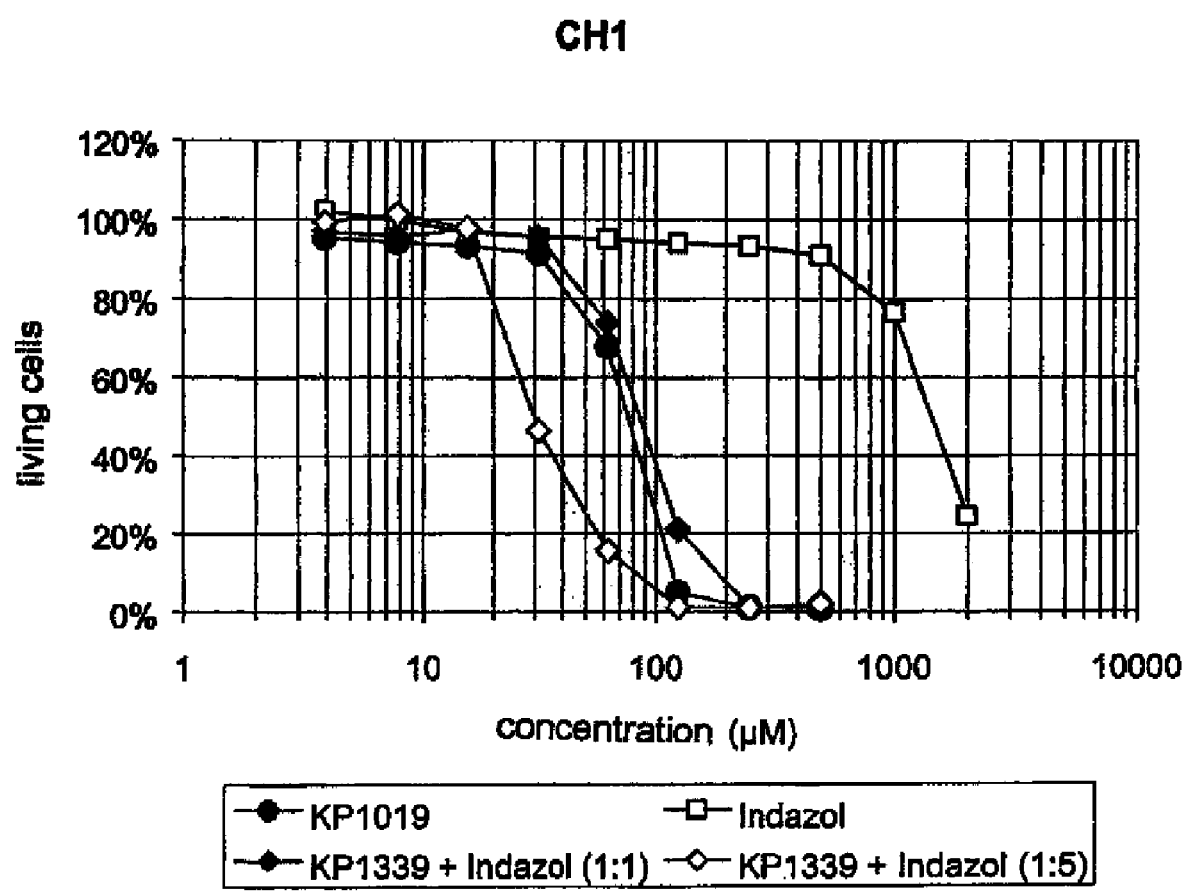
FIG. 4 shows a comparison of the cytotoxic effects of KP 1019, indazol, and of mixtures of KP 1339 and indazol in the molar ratios of 1:1 and 1:5 (administered as a solution in a conventional cell culture medium MEM, supplemented with 10% of fetal bovine serum, without the addition of organic solvents or dissolving agents) on the human line of tumor cells CH1 (ovarian carcinoma) in the MTT assay with continuous 96 hour exposure to the active substance.

The manufacture of the compounds of the general formula (I) can take place according to the instructions described in WO 97/36595. Furthermore, the manufacture of the compounds of the general formula (III) can take place as shown in *J. Cancer Res. Clin. Oncol.* 1992, 118(3), pp. 195-200. The manufacture of the compounds of the formulae (II) and (IV) takes place according to known methods.

DETAILED DESCRIPTION OF THE INVENTION

This object is solved by a composition (A), obtained by reacting a complex compound of the general formula (I)

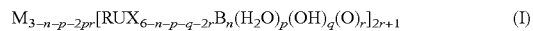
$$M_{3-n-p-2pr}[RUX_{6-n-p-q-2r}B_n(H_2O)_p(OH)_q(O)_r]_{2r+1} \quad (I)$$

where

M is an alkali metal cation or ammonia,

B is a monocyclic or multi-cyclic basic heterocycle with one or more nitrogen atoms, X is a halide, pseudo-halide, $HCO_3^-$, or $RCOO^-$, in which R is a substituted or unsubstituted $C_1$-$C_6$-alkyl or $C_2$-$C_6$-alkenyl or a substituted or unsubstituted aryl, n=1 or 2, p, q=0 or 1 or (if r=0.5) 0 or 0.5, and r=0 or 0.5, with a compound of the formula (II)

$$B'(HX')_s \quad (II)$$

where

B' is a monocyclic or multi-cyclic basic heterocycle with one or more nitrogen atoms, X' is a halide, pseudo-halide, $HCO_3^-$, or $RCOO^-$, in which R is hydrogen or a substituted or unsubstituted $C_1$-$C_6$- alkyl or $C_2$-$C_6$-alkenyl or a substituted or unsubstituted aryl, phosphate, sulphate and/or acetate, and s is an integer of 1 or more.

The object is also solved by a composition (B), obtained by mixing a complex compound of the general formula (III)

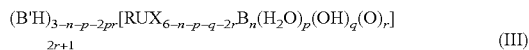

where each B, B' is a monocyclic or multi-cyclic basic heterocycle with one or more nitrogen atoms, X is a halide, pseudo-halide, $HCO_3^-$, or $RCOO^-$, in which R is a substituted or unsubstituted $C_1$-$C_6$-alkyl or $C_2$-$C_6$-alkenyl or a substituted or unsubstituted aryl, n=1 or 2, p, q=0 or 1 or (if r=0.5) 0 or 0.5, and r=0 or 0.5, with a compound of the formula (IV)

where

M is an alkali metal cation or ammonia and

X' is a halide, pseudo-halide, $HCO_3^-$, or $RCOO^-$, in which R is hydrogen or a substituted or unsubstituted $C_1$-$C_6$-alkyl or $C_2$-$C_6$-alkenyl or a substituted or unsubstituted aryl, phosphate, sulphate or acetate.

B and/or B' in the formulae (I), (II) or (III) can be purine, adenine, guanine, cytosine, indazol, imidazol, pyrazol, pyridine, pyrimidine, pyridazine, pyrrol, tetrazol and/or triazine which can be substituted by one or more substituents, selected from the group consisting of: hydroxyl, amino, halogen, $C_1$-$C_4$-alkyl, $C_2$-$C_4$-alkenyl, $C_1$-$C_4$-alkyl mercapto, formyl-, $C_1$-$C_4$-alkoxy carbonyl, $C_1$-$C_4$-alkoxy carbonyl-$C_1$-$C_4$-alkylene, di-$C_1$-$C_4$-alkyl-amino, di-$C_1$-$C_4$-alkyl-amino-$C_1$-$C_4$-alkylene, di-$C_1$-$C_4$-alkyl-amino-carbonyl, di-$C_1$-$C_4$-alkyl-amino-carbonyl-$C_1$-$C_4$-alkylen, hydroxy imino methine, phenyl, benzyl, benzoyl, pyrrolidino, piperidino, pyrrol-1-yl and pyrrol-1-yl-$C_1$-$C_4$-alkylene, or a ring

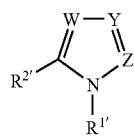

where $R^{1'}$ is hydrogen, sodium, $C_1$-$C_4$-alkyl or phenyl and $R^{2'}$ is hydrogen, $C_1$-$C_4$-alkyl, amino or phenyl, or $R^{1'}$ and $R^{2'}$ together represent a group —$(CH_2)_s$- where s is an integer from 4 to 8, W is nitrogen or $CR^{3'}$, where $R^{3'}$ is a hydrogen, $C_1$-$C_4$-alkyl, amino or phenyl, preferably hydrogen or methyl, Y is nitrogen or $CR^{4'}$ where $R^{4'}$ is a hydrogen, $C_1$-$C_4$-alkyl, amino or phenyl, preferably hydrogen or methyl, and Z is nitrogen or $CR^{5'}$ where $R^{5'}$ is a hydrogen, $C_1$-$C_4$-alkyl, amino or phenyl, preferably hydrogen or methyl, whereby the ring is bonded to the basic heterocycle B or B' by at least one of the substituents $R^{1'}$ and $R^{2'}$.

Preferably at least one of the groups $R^{3'}$, $R^{4'}$ or $R^{5'}$ is a hydrogen.

Preferably the at least one substituent is selected from the group consisting of chlorine, diethylamino, dimethylamino and pyrrol-1-yl-methyl.

In a preferred embodiment B and/or B' in the formulae (I), (II) or (III) can be 1-methylimidazol, 4-methylimidazol, 4-methylpyrazol, 1-sodium pyrazol, 1-phenyltetrazol or 5-phenyltetrazol which can be substituted, preferably in position 4 by one or more substituents, as defined above.

In a further preferred embodiment B and/or B' in the formulae (I), (II) or (III) are imidazol, pyrazol, triazol or indazol, with imidazol, triazol or indazol being particularly preferred, but more preferably triazol or indazol, especially indazol.

B' and B can be the same, i.e. they can represent the same heterocycle.

Furthermore, M in the formulae (I) and (IV) is preferably lithium, sodium or potassium, especially sodium.

In the preferred embodiments X and/or X' in the formulae (I), (II), (III) or (IV) are chlorine or bromine, especially chlorine. In another preferred embodiment X' in the composition (A) or (B) corresponds to X.

The molar ratio of the compound of formula (I) to the compound of formula (II) in the composition (A) according to the invention is preferably <1, a ratio between 1:1.1 and 1:10 is particularly preferred, and especially 1:2 and 1:5.

The molar ratio of the compound of formula (III) to the compound of formula (IV) in the composition (B) according to the invention is preferably a ratio between 1:2 and 1:30, with 1:5 and 1:15 being particularly preferred, with 1:10 being especially preferred.

In a preferred embodiment the compound of formula (I) is sodium trans-tetrachlorobis(1 H-indazol)-ruthenate(III).

The compound of formula (II) is preferably indazolium hydrochloride.

The compound of formula (III) is preferably indazolium trans-[tetrachlorobis-(indazol)ruthenate(III)].

The compound of formula (IV) is preferably sodium chloride.

The composition (A) or (B) according to the invention can be present in the form of an aqueous solution.

The composition (B) can be obtained by attrition of a compound of the formula (III) with a compound of formula (IV) in mortars or mills, such as air stream or ball mills.

It was surprisingly found that the availability of a compound of the general formula (III) in aqueous solution can be improved by mixing with a compound of the general formula (IV) while retaining the composition (B).

It was also surprisingly found that a compound of the general formula (I), which is slightly soluble in water and lyophilisable, offers suitable formulation methods by reaction with a compound of the general formula (II) to form a composition (A) according to the invention suitable for the treatment of cancer illnesses (see Examples 1-3 and FIGS. 1-4).

Furthermore, the object of the invention is solved by a medicament which contains the compositions (A) and/or (B) according to the invention.

The compositions (A) and/or (B) can furthermore be employed in the manufacture of a medicament for the prophylaxis and/or treatment of cancer illnesses.

The medicament according to the invention is described in more detail as follows.

The medicaments according to the invention are primarily administered intravenously, but also intramuscularly, intraperitoneally, subcutaneously or perorally. External application is also possible. Administration through intravenous injection or infusion is preferred.

The pharmaceutical preparations are produced by known methods whereby the composition according to the invention is used on its own or, where necessary in combination with suitable pharmaceutical carrier substances. If the pharmaceutical preparations contain pharmaceutical carrier substances as well as the active substance, the content of active substance in these mixtures is 0.1 to 99.5%, preferably 0.5 to 95% by weight of the total mixture.

The active substance can be applied in any suitable formulation with the requirement that the formation or maintenance of a sufficient level of active substance is ensured. This can, for example, be achieved through oral or parenteral administration in suitable doses. Advantageously, there is the pharmaceutical preparation of the active substance in the form of standard doses, which are adapted to the desired administration. A standard dose may be, for example, a tablet, dragée, capsule, suppository or a measured volume of a powder, a granulate, solution, emulsion or suspension.

A "standard dose" in the sense of this invention is taken to mean a physically determined unit which contains an individual quantity of the active constituent in combination with a pharmaceutical carrier substance and its content of active substance corresponds to a fraction or multiple of a therapeutic single dose. A single dose preferably contains the quantity of active substance which is administered during an application and which normally corresponds to a whole, half, third or quarter of the daily dose. If only a fraction, such as half or quarter of the standard dose is needed for a single therapeutically administered dose, then the standard dose is advantageously divisible, e.g. in the form of a tablet with a dividing groove.

The medicaments according to the invention can, if they are available in standard doses and intended for application, e.g. on persons, contain about 0.1 to 500 mg, preferably 10 to 200 mg and particularly 50 to 150 mg of active substance.

Generally in human medicine, the active substance(s) are administered in a daily dose of 0.1 to 5, preferably 1 to 3 mg/kg of body weight, where necessary in the form of a number, preferably 1 to 3, of single intakes for achieving the desired results. A single intake contains the active substance(s) in quantities of 0.1 to 5, preferably 1 to 3 mg/kg of body weight. With oral treatment similar dosages can be applied.

The therapeutic administration of pharmaceutical preparations can occur 1 to 4 times daily at specified or varying time points, e.g. in each case before meals and/or in the evening. However, it may be necessary to deviate from the quoted dosages depending on the type, body weight and age of the individual to be treated, the type and severity of the illness, the type of preparation and the application of the pharmaceutical preparations as well as the time period or interval within which the administration occurs. Consequently, in some cases it may be sufficient to use less than the amount of active substance mentioned above, whereas in other cases the above listed quantities of active substance must be exceeded. It may also be practicable to administer the pharmaceutical preparations only once or at intervals of several days.

The specification of the necessary optimum dosage and type of application of the active substance can be made by any specialist based on his specialist knowledge.

The pharmaceutical preparations normally comprise the composition according to the invention and non-toxic, pharmaceutically compatible medication carriers which are employed as admixtures or diluting agents for example in solid, semi-solid or liquid form or as a means of enclosure, for example in the form of a capsule, a tablet coating, a bag or another container for the therapeutically active constituent. A carrier material may, for example, act as an agent for the ingestion of the medicament by the body, as a formulation agent, sweetener, taste modifier, colorant or as preservative.

For oral application, for example, tablets, dragées, hard and soft capsules, for example of gelatine, dispersible powder, granulate, aqueous and oily suspensions, emulsions, solutions and syrups can be employed.

Tablets can contain inert binding agents, e.g. calcium carbonate, calcium phosphate, sodium phosphate or lactose; granulation and distributing agents, e.g. maize starch or alginates; binding agents, e.g. starch, gelatine or arabine; and lubricating agents, e.g. aluminium or magnesium stearate, talcum or silicone oil. They can also be provided with a coating which is produced such that it causes delayed release and resorption of the pharmaceutical preparation in the gastro-intestinal tract, so that, for example, improved compatibility, assimilation or retardation is achieved. Gelatine capsules may contain the pharmaceutical substance with a solid, e.g. calcium carbonate or kaolin or an oily, e.g. olive, peanut or paraffin oil dilution agent.

Aqueous suspensions can contain suspension agents, e.g. sodium carboxymethyl cellulose, methyl cellulose, hydroxypropyl cellulose, sodium alginate, polyvinyl pyrrolidon, traganth rubber or arabine; dispersant or wetting agents, e.g. polyoxyethylene stearate, heptadeca-ethylene-oxycatanol, polyoxyethylene sorbitol-monooleate, or lecithin; preservatives, e.g. methyl- or propylhydroxy-benzoate; taste modifiers; sweeteners, e.g. saccharose, lactose, sodium cyclamate, dextrose, invert sugar syrup.

Oily suspensions may be, for example, peanut, olive, sesame, coconut or paraffin oil and thickening agents, such as beeswax, high melting point wax or cetyl alcohol; also sweeteners, taste modifiers and antioxidants.

Powder and granulates dispersible in water may contain the composition according to the invention in a mixture with dispersing, wetting and suspension agents, e.g. those mentioned above as well as with sweeteners, taste modifiers and colorants.

Emulsions can, for example, contain olive, peanut or paraffin oil as well as emulsifying agents such as arabine, traganth rubber, phosphatides, sorbitan monooleate, polyoxyethylene sorbitan monooleate and sweeteners and taste modifiers.

Aqueous solutions can contain preservatives, e.g. methyl- or propylhydroxybenzoates; thickening agents; taste modifiers; sweeteners, e.g. saccharose, lactose, sodium cyclamate, dextrose, invert sugar syrup as well as taste modifiers and colorants.

For the parenteral application of pharmaceutical substances sterile injectable aqueous solutions, isotonic salt solutions or other solutions can be used.

As a menstruum for infusion any suitable solution can be used. Water and Haemaccel® are preferred.

The method according to the invention for the production of the composition (A) includes the reaction of a complex compound of the formula (I) with a compound of the formula (II). The reaction preferably takes place in an aqueous solution.

The method according to the invention for the production of the composition (B) includes mixing a complex compound of the formula (III) with a compound of the formula (IV). Here, a compound of the formula (III) is put through attrition with a compound of the formula (IV), e.g. in the mortar or in ball mills.

Furthermore, a kit (A) is made available which comprises a receptacle with a compound of the formula (I)

$$M_{3-n-p-2pr}[RuX_{6-n-p-q-2r}B_n(H2O)_p(OH)_q(O)_r]_{2r+1} \quad (I)$$

where

M is an alkali metal cation or ammonia,

B is a monocyclic or multi-cyclic basic heterocycle with one or more nitrogen atoms, X is a halide, pseudo-halide, $HCO_3^-$, or $RCOO^-$, in which
R is a substituted or unsubstituted $C_1$-$C_6$-alkyl or $C_2$-$C_6$-alkenyl or a substituted or unsubstituted aryl,
n=1 or 2,
p, q=0 or 1 or (if r=0.5) 0 or 0.5, and
r=0 or 0.5,
as well as a receptacle with a compound of the formula (II)

(II)

where
B' is a monocyclic or multi-cyclic basic heterocycle with one or more nitrogen atoms,
X' is a halide, pseudo-halide, $HCO_3^-$, or $RCOO^-$, in which R is hydrogen or a substituted or unsubstituted $C_1$-$C_6$-alkyl or $C_2$-$C_6$-alkenyl or a substituted or unsubstituted aryl, phosphate, sulphate, acetate, and
s is an integer of 1 or more.

In a preferred embodiment X' in kit (A) is the same radical as X and B the same radical as B'.

Also, a kit (B) is made available which comprises a receptacle with a compound of the formula (III)

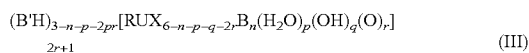

(III)

where
B, B' is a monocyclic or multi-cyclic basic heterocycle with one or more nitrogen atoms,
X is a halide, pseudo-halide, $HCO_3^-$, or $RCOO^-$, in which
R is a substituted or unsubstituted $C_1$-$C_6$-alkyl or $C_2$-$C_6$-alkenyl or a substituted or unsubstituted aryl,
n=1 or 2,
p, q=0 or 1 or (if r=0.5) 0 or 0.5, and
r=0 or 0.5,
as well as a receptacle with a compound of the formula (IV)

MX'    (IV)

where
M is an alkali metal cation or ammonia,
X' is a halide, pseudo-halide, $HCO_3^-$, or $RCOO^-$, in which
R is hydrogen or a substituted or unsubstituted $C_1$-$C_6$-alkyl or $C_2$-$C_6$-alkenyl or a substituted or unsubstituted aryl, phosphate, sulfate or acetate.

To the radicals X, X', B and B' the same applies as for the above kit (A).

In the following the kit (A) according to the invention is explained in more detail.

In the clinic the application of the composition (A) according to the invention on the patient can take place through the provision of a kit which contains an ampoule with a compound of the formula (I), preferably as sodium salt, as well as separately an infusion solution which contains an equimolar or also a higher concentration of a compound of the formula (II), preferably as hydrochloride. Before the application on the patient, the content of the ampoule dissolved in water can be injected into the infusion bottle. In this way the composition (A) according to the invention is formed which can then be immediately used on the patient.

In the following the kit (B) according to the invention is explained in more detail.

In the clinic the application of the composition (B) according to the invention on the patient can take place through the provision of a kit which contains an ampoule (1) with a compound of the formula (III), preferably as indazolium salt, as well as separately an ampoule (2) with a compound of the formula (IV), e.g. sodium chloride, as well as a menstruum for the infusion. Before the application on a patient the content of the ampoule (1) is put through attrition, e.g. in a mortar with the content of ampoule (2) under retention of the composition (B) according to the invention. Then the compound (B), dissolved in the menstruum for infusion, can be injected into the infusion bottle and immediately used on the patient.

In the following the invention is explained based on some examples.

EXAMPLE 1

The compound sodium trans-[RuCl$_4$(ind)$_2$], KP1339, which is easily water-soluble and lyophilisable was reacted with indazolium hydrochloride to form a composition (A) according to the invention, containing indazolium trans-[tetrachlorobis(1H-indazol)-ruthenate(III)] (KP 1019) and sodium chloride (see FIG. 1).

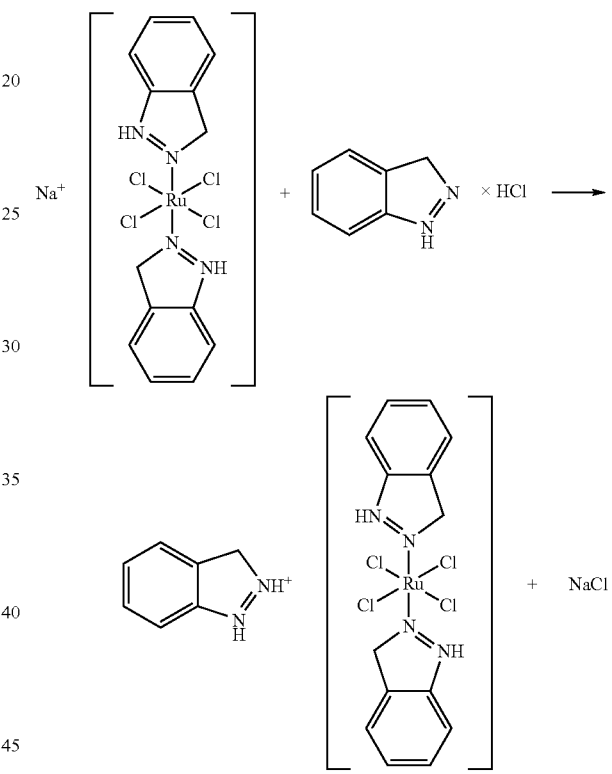

FIG. 1: Formation of a composition (A) according to the invention, containing indazolium trans-[tetrachlorobis(1H-indazol)-ruthenate(III)] (KP 1019) and sodium chloride, by the reaction of KP 1339 and indazolium hydrochloride.

EXAMPLE 2

Cytotoxicity investigations were carried out on the composition obtained according to Example 1. The composition was obtained by reacting the sodium salt KP1339, which exhibits a water-solubility of more than thirty times higher than KP 1019, with indazolium hydrochloride in the infusion solution immediately before administration.

Since experiments on the stem cells of human solid tumors which were bred on as nude mice xenografts, and on continuous human tumor cell lines corresponded in showing that KP 1339 in vitro exhibits clearly weaker antiproliferative effectiveness than KP 1019, clarification was obtained in further experiments of how far the stronger activity of KP 1019 can be restored by the addition of indazol to solutions of KP 1339.

The tumor inhibiting activity of the equimolar mixture of KP 1339 and indazol proved to be identical to that of the original KP 1019 (see FIGS. 1 and 2), whereas pure KP 1339 was three to four times less effective than KP 1019. This has been confirmed on two tumor cell lines (SW480, CH1) and reproduced four times. In these experiments the lower effectiveness of KP 1339 in comparison to KP 1019 was confirmed.

EXAMPLE 3

In the first experiments with compositions which had been obtained by reacting KP 1339 with indazolium hydrochloride in the molar ratio of 1:1, it could be shown as a result that the cytotoxic activity of the original KP 1019 was attained. Further experiments gave insight into the manner in which an excess of indazol affected the cytotoxicity.

The cytotoxic effects of KP 1019 and combinations of KP 1339 and indazol in different molar ratios (administered as solution in the conventional cell culture medium MEM, supplemented with 10% fetal bovine serum, without the addition of organic solvents or dissolving agents) have been comparatively investigated on the human line of tumor cells SW480 (colon carcinoma) and CH1 (ovarian carcinoma) in the MTT assay under the application of a continuous 96 hour exposure to the active substance.

It has been surprisingly shown that the tumor inhibiting activity can be further increased by the addition of an excess of indazol. A mixture of KP 1339 and indazol in the molar ratio of 1:5 gave a two to five times increase in the cytotoxicity compared to KP 1019 (see FIGS. 3 and 4). A molar ratio of 1:2 is already sufficient to exceed the effectiveness of the original KP 1019. Indazol itself only exhibits a cytotoxic effect in higher concentrations (>1 mM). The increase in the tumor inhibiting activity of the solutions which contain an excess of indazol cannot therefore be explained by a purely additive effect of the components, but is rather attributable either to a synergistic effect, a positive effect of the free indazol on the stability of the complex or on an unknown mechanism. The discontinuous trace of the dosage/effect curve on the cell line SW480 which proved to be strictly reproducible in five independent experimental runs indicates a complex interaction between KP 1339 and indazol.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A process of making a composition comprising a mixture of:
   (i) a compound of the general formula (III):

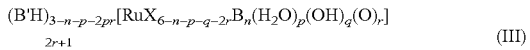

(III)

wherein
   B and B' are independently a monocyclic or multi-cyclic basic heterocycle chosen from imidazole, pyrazol, triazol, and indazol,
   X represents a halide, pseudo-halide, $HCO_3^-$, or $RCOO^-$ in which R represents a substituted or unsubstituted $C_1$-$C_6$-alkyl or $C_2$-$C_6$-alkenyl or a substituted or unsubstituted aryl, n=1 or 2, r=0, and each of p and q=0 or 1, or r=0.5 and each of p and q=0 or 0.5; and (ii) a compound of the formula (IV):

$$MX' \quad (IV)$$

wherein
   M represents an alkali metal cation or ammonia, and
   X' represents a halide, pseudo-halide, $HCO_3^-$, or $RCOO^-$ in which R is hydrogen or a substituted or unsubstituted $C_1$-$C_6$-alkyl or $C_2$-$C_6$-alkenyl or a substituted or unsubstituted aryl, phosphate, sulphate or acetate, said process comprising:
   reacting a compound of the formula (I)

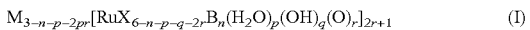

(I)

with a compound of the formula (II)

(II)

wherein
   s is an integer of 1 or more, and M, B, X, B', X', n, p, q, and r are as defined above.

2. The process according to claim 1, wherein the molar ratio of the compound of the formula (I) to the compound of the formula (II) is less than 1.

3. The process according to claim 1, wherein the molar ratio of the compound of the formula (I) to the compound of the formula (II) is from 1:1.1 to 1:10.

4. The process according to claim 1, wherein the molar ratio of the compound of the formula (I) to the compound of the formula (II) is from 1:2 to 1:5.

5. The process according to claim 1, wherein said B and B' are independently indazol.

6. The process according to claim 1, wherein said X and X' are halide.

7. The process according to claim 1, wherein said M represents an alkali metal cation.

8. A process of making a composition comprising a mixture of indazolium trans-[tetrachlorobis(1H-indazol)-ruthenate(III)], and sodium chloride, said process comprising reacting sodium trans-[tetrachlorobis(1H-indazol)-ruthenate(III)] with indazolium hydrochloride under conditions to form said composition.

9. The process according to claim 8, wherein the molar ratio of sodium trans-[tetrachlorobis(1H-indazol)-ruthenate(III)] and indazolium hydrochloride is less than 1.

10. The process according to claim 8, wherein the molar ratio of sodium trans-[tetrachlorobis(1H-indazol)-ruthenate(III)] and indazolium hydrochloride is from about 1:1.1 to about 1:10.

* * * * *